(12) United States Patent
Umbarkar et al.

(10) Patent No.: US 9,409,854 B2
(45) Date of Patent: Aug. 9, 2016

(54) LIQUID PHASE NITRATION OF AROMATICS USING SOLID ACID CATALYST

(71) Applicant: COUNCIL OF SCIENTIFIC & INDUSTRIAL RESEARCH, New Delhi (IN)

(72) Inventors: Shubhangi Bhalchandra Umbarkar, Pune (IN); Mohan Keraba Dongare, Pune (IN); Ankush Venkatrao Biradar, Pune (IN); Atul Balasaheb Kulal, Pune (IN); Trupti Vyankatesh Kotbagi, Pune (IN); Ashvini Ramesh Bhosale, Pune (IN); Macchindra Gulabrao Chandgude, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/895,867

(22) PCT Filed: Jun. 3, 2014

(86) PCT No.: PCT/IN2014/000375
§ 371 (c)(1),
(2) Date: Dec. 3, 2015

(87) PCT Pub. No.: WO2014/195973
PCT Pub. Date: Dec. 11, 2014

(65) Prior Publication Data
US 2016/0145191 A1 May 26, 2016

(30) Foreign Application Priority Data
Jun. 3, 2013 (IN) .......................... 1662/DEL/2013

(51) Int. Cl.
| | | |
|---|---|---|
| *C07C 205/00* | (2006.01) | |
| *C07C 201/08* | (2006.01) | |
| *C07B 43/02* | (2006.01) | |
| *B01J 23/30* | (2006.01) | |
| *B01J 21/08* | (2006.01) | |
| *B01J 37/02* | (2006.01) | |
| *B01J 37/04* | (2006.01) | |
| *B01J 37/08* | (2006.01) | |

(52) U.S. Cl.
CPC ............... *C07C 201/08* (2013.01); *B01J 21/08* (2013.01); *B01J 23/30* (2013.01); *B01J 37/0236* (2013.01); *B01J 37/04* (2013.01); *B01J 37/08* (2013.01); *C07B 43/02* (2013.01)

(58) Field of Classification Search
CPC .. C07C 201/08; C07C 205/11; C07C 205/12; C07C 205/20; B01J 23/30; B01J 21/08; B01J 35/1019
USPC .......................................... 568/939
See application file for complete search history.

(56) References Cited

FOREIGN PATENT DOCUMENTS

| | | |
|---|---|---|
| CN | 102627564 A | 8/2012 |
| WO | 2008/075901 A1 | 6/2008 |

OTHER PUBLICATIONS

A.S. Khder et al.,Selective nitration of phenol over nanosized tungsten oxide supported on sulfated SnO2 as a solid acid catalyst, Article, 2009, 8 pp., Chemistry Department, Faculty of Science, Mansoura University, Mansoura, Egypt.
Sanyo M. Mathew et al., Regioselective nitration of cumene to 4-nitro cumene using nitric acid over solid acid catalyst, article, 2006, 5 pp., Catalysis Division, National Chemical Laboratory, India.
S. B. Umbarkar, et al. Vapor phase nitration of benzene using mesoporous MoO3/SiO2 solid acid catalyst, Journal, Mar. 28, 2006, 6 pp., The Royal Society of Chemistry, India.
Filippo Sornma, et al., Oxidation of geraniol and other substituted olefins with hydrogen peroxide using n1esoporous, sol-gel-n1ade tungsten oxide-silica mixed oxide catalysts, Journal, 2004, 8 pp., Dipartimento di Chimica, Universita di Venzia and Consorzio INTEM, Venzia Italy.

*Primary Examiner* — Jafar Parsa
(74) *Attorney, Agent, or Firm* — Banner & Witcoff, Ltd.

(57) ABSTRACT

The present invention discloses an improved process for the liquid phase nitration of aromatic compounds catalyzed by WO3 supported on mesoporous silica support, at low temperature, with high conversion and selectivity.

8 Claims, 1 Drawing Sheet

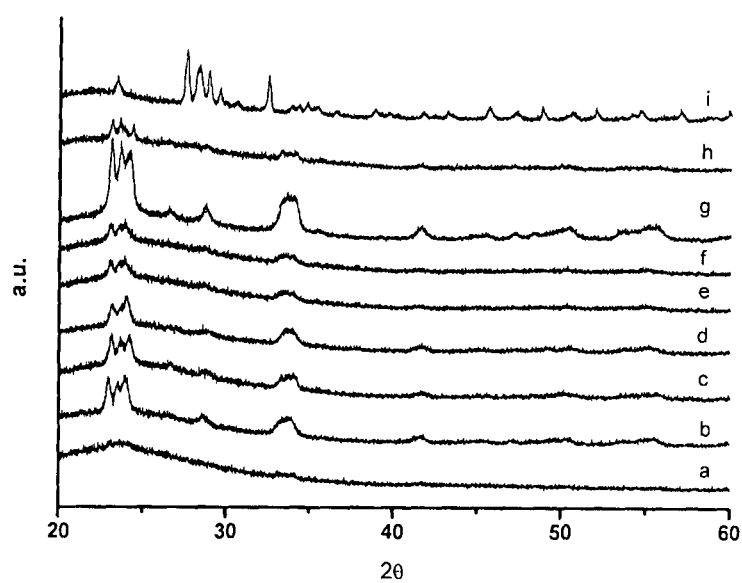

LIQUID PHASE NITRATION OF AROMATICS USING SOLID ACID CATALYST

CROSS-REFERENCE TO RELATED APPLICATIONS

The present application is a U.S. National Phase filing of International Application No. PCT/IN2014/000375, filed on Jun. 3, 2014, designating the United States of America and claiming priority to India Patent Application No. 1662/DEL/2013, filed Jun. 3, 2013, and this application claims priority to and the benefit of the above-identified applications, which are both incorporated by reference herein in their entireties.

TECHNICAL FIELD OF THE INVENTION

The present invention relates to an improved process for the liquid phase nitration of aromatic compounds catalysed by $WO_3$ supported on mesoporous silica support, at low temperature, with high conversion and selectivity.

BACKGROUND AND PRIOR ART OF THE INVENTION

Aromatic nitro compounds are an important class of compounds used in industry for the manufacture of dyes, pharmaceuticals and fine chemicals. A more common aromatic nitro compound, nitrobenzene, is very much used as processing solvents in specific chemical reactions. The conventional process of nitrating aromatic compounds includes a nitrating mixture which is concentrated sulphuric acid and fuming nitric acid. During the use of nitrating mixture, a large quantity of dilute sulphuric acid is generated as waste which needs to be concentrated for its reuse which is highly energy intensive process or has to be disposed which poses environmental problems. Thus nitration of aromatic compounds is environmentally hazardous industrial process. Further, selectivity of desired product is low. To make the nitration process more economical, environment friendly and to minimize or avoid use of sulphuric acid researchers among all over the world are working around or have developed alternate methods for nitration process. Accordingly, considerable efforts have been put into developing of the heterogeneously catalysed liquid or vapor phase nitration of aromatic compounds using solid acid catalysts, few of which are appended below.

Vapour phase nitration of aromatic compounds, benzene and toluene at temperature ranging from about 275° C. to about 310° C. and silica gel as catalyst is described in McKee and Wilhelm, Industrial and Engineering Chemistry, 28(6), 662-667 (1936).

U.S. Pat. No. 2,431,585 describes vapor phase nitration of aromatic hydrocarbons at temperature from 130° C. to 430° C., using metal phosphates of calcium, iron, magnesium and solid supported phosphoric acid catalysts.

U.S. Pat. No. 4,551,568 describes the vapor phase nitration of benzene over solid mixed oxide catalyst comprising $WO_3$ and $MoO_3$, which exhibited a fairly high and stable activity.

U.S. Pat. No. 3,966,830, JP-58-157748 and U.S. Pat. No. 4,426,543 describe the nitration of aromatics using zeolite catalysts.

EP0092372 disclose a process for the gas-phase nitration of benzene which comprises treating benzene with nitrating agent comprising of an oxide of nitrogen i.e $NO_2$ or $N_2O_4$ in the presence of a solid catalyst composed of an acidic mixed oxide containing at least one of $WO_3$, $MoO_3$ and $TiO_2$ and optionally containing $SiO_2$ and/or $ZnO$.

U.S. Pat. No. 6,791,000 disclose vapor phase nitration of benzene, which comprises nitrating benzene with nitric acid over a molybdenum silica catalyst.

Article titled "Liquid phase nitration of benzene over supported ammonium salt of 12-molybdophosphoric acid catalysts prepared by sol-gel method" by Gong S, Liu L, et. al in J Hazard Mater. 2010 Jun. 15; 178(1-3):404-8 disclose liquid phase nitration of benzene with 65% nitric acid as nitrating agent over silica supported ammonium salt of 12-molybdophosphoric acid catalysts.

U.S. Pat. No. 6,362,381 disclose nitration of aromatic hydrocarbon in the liquid phase with an oxide of nitrogen selected from $NO$, $N_2O_3$, $NO_2$ and $N_2O_4$ and with an oxygen-containing gas stream in the presence of a heterogeneous oxidic catalyst. The catalyst is an oxygen compound of one or more elements of groups IIIa, IVa, IIIb or IVb of the Periodic Table of the elements. CN101412677 disclose selective nitration of chlorobenzene in liquid phase using nitric acid and in presence of $WO_3/ZrO_2$ acid catalyst.

Although the use of solid acid catalyst show good catalytic property in the nitration process, however, the complicated nature of the catalysts and deactivation of solid catalysts during the process needs to be addressed. Moreover, the vapor phase nitration of aromatics has the limitations of low conversions, low space-time yield, low yield, short catalyst life and contamination of the products by undesirable by-products. Further, reaction in vapour phase requires high temperature and may lead to di-nitration explosion.

Furthermore, since the acids used in the nitrating process are concentrated, the material of construction for the plant is quite costly increasing the overall basic investment. The safety aspects involved in handling these concentrated acids in large quantities also needs to be implemented while operating such plants.

It has been observed that nitration with undiluted nitric acid generates water that leads to the dilution of the nitric acid, so that the concentration of the nitronium ions and thus the reaction rates are reduced. It also gives a lower selectivity due to the oxidation of the aromatic substrate.

In view of the market demand for aromatic nitro compounds a more beneficial process for producing the same is still desired.

OBJECTS OF THE INVENTION

Main objective of the present invention is to provide liquid phase nitration of aromatics using a novel solid acid catalyst that gives higher activity, selectivity, and high stability.

Another object of the present invention is to develop a process using a solid acid catalyst that can be carried out at low temperature which can control selectivity and avoid the use of sulphuric acid.

SUMMARY OF THE INVENTION

Accordingly, present invention provides a liquid phase nitration of aromatic compounds using solid acid catalyst and the said process comprising the steps of:
  i. refluxing a solution of aromatic compound and the solid acid catalyst in an organic solvent under nitrogen atmosphere at a temperature in the range of 80-110° C. for period in the range of 2 to 10 hr followed by drop wise addition of 30-98% $HNO_3$ preferably 70% with the removing of the water formed during the reaction azeotropically.

In an embodiment of the present invention, solid acid catalyst used is tungsten oxide ($WO_3$) supported on mesoporous silica having BET surface area in the range of 367 to 397 $M^2/g$.

In another embodiment of the present invention, the aromatic compound is selected from monocyclic or polycyclic aromatic compounds such as benzene, xylene, toluene, naphthalene, phenanthrene, phenols or heteroaryls.

In yet another embodiment of the present invention, the aromatic compounds are selected from monocyclic or polycyclic aromatic compounds which may be monosubstituted or polysubstituted by, for example, nitro, nitroso, halogen, hydroxyl, alkoxy, aryloxy, carboxyl, alkylcarbonyloxy, arylcarbonyloxy, acylamino, alkylsulfonyl, arylsulfonyl, alkylsulfoxyl, arylsulfoxyl, sulfo, cyano and/or C1-C17 alkyl groups, preferably by nitro, halogen, cyano and/or C1-C17 alkyl groups. Amino, alkylamino or dialkylamino groups, low-valency sulfur- or phosphorus-containing substituents and other readily oxidizable or nitratable groups are unsuitable for the purposes of a selective nitration of the aromatic ring. Preferred aromatic hydrocarbons are unsubstituted or substituted benzene, xylenes, toluene, naphthalene, phenols, biphenyl, anthracene and phenanthrene, heteroaryls.

In yet another embodiment of the present invention, the catalyst is used in the molar ratio of 0.009 to 0.1 per mole of the aromatic compound used.

In yet another embodiment of the present invention, the organic solvent is selected from solvents with a boiling point in the range of 80-110° C. such as acetonitrile, 1,2 dichloroethane or dioxane.

In yet another embodiment, present invention provides a sol-gel process for preparation of the solid acid catalyst comprising the steps of:
  i. mixing silica-40 and C1 to C6 alcohol with stirring for a period in the range of 1 to 3 hr to obtain a solution;
  ii. adding drop wise aqueous metatungstate salt solution in the solution as obtained in step (i);
  iii. stirring the mixture as obtained in step (ii) for a period in the range of 1 to 3 hr followed by addition of 2-10% ammonium hydroxide solution to obtain a white gel;
  iv. drying the gel as obtained in step (iii) for period in the range of 2 to 24 hr followed by calcining for period in the range of 2 to 6 hr at temperature in the range of 450 to 500° C. at the rate of 5° C. per min to obtain the solid acid catalyst.

In yet another embodiment of the present invention, the metatungstate salt is selected from alkali, alkaline earth metals or ammonium meta tungusted salt.

In yet another embodiment, present invention provides the sol-gel process comprises:
  i. reacting the solution of tungstic acid in water with 45 to 55% aq. hydrogen peroxide followed by addition of 20 to 30% ammonia to obtain a solution;
  ii. Adding drop wise solution of step (i) to a mixture of silica-40 and C1 to C6 alcohol, stirring, adding 2-10% ammonia to obtain a white gel; and
  iii. drying and calcining at about 500° C. to yield the desired product.

BRIEF DESCRIPTION OF THE FIGURES

FIG. 1 depict XRD patterns of catalysts prepared as given in example a) 1; b) 2; c) 3; d) 4; e) 5; f) 6; g) 7; h) 8; i) 9.

DETAILED DESCRIPTION OF THE INVENTION

The present invention discloses environment friendly, cost effective, liquid phase nitration of aromatic compounds using solid acid catalyst, with high conversion and selectivity.

The instant liquid phase nitration of the aromatic compound avoids the use of sulphuric acid or the nitrating mixture thus avoiding any hazardous waste, and use of costly material of construction for the process plant. The process uses commercial nitric acid of 65-70% concentration as nitrating agent and the nitration is carried out in presence of solid acid catalyst at low temperature, due to which the instant process is cost effective and simple.

The solid acid catalyst is recyclable, easy to work with high selectivity. It can eliminate the problem associated with the formation of water in nitration reaction. Nitration using Bronsted acid produces water which dilutes the concentration of the acid which lowers the efficiency of the nitrating acid. Thus removal and disposal of large amount of diluted acid left after the reaction is not only tedious but costly as well as not environmental friendly. Thus, the present inventors have developed an alternate, beneficial liquid phase nitration of aromatic compounds in presence of a novel solid acid catalyst which is stable at low temperature.

The catalyst used in the process comprises tungsten oxide ($WO_3$) supported on mesoporous silica support. The catalyst provides for selective nitration of aromatic compounds and does not degrade during the reaction process. The optimum catalytic activity is achieved by controlling the conditions during preparation of catalyst. Further, the catalyst used in the instant invention are acidic in nature and have acidity <3. The BET surface area of the catalyst 367 to 397 $M^2/g$.

The present invention provides an improved, industrially feasible, cost effective liquid phase nitration of aromatic compounds characterized in that said process is catalysed by tungsten oxide ($WO_3$) supported on mesoporous silica support, with high conversion and selectivity, comprising;
  i. Refluxing a solution of aromatic compound and said solid acid catalyst under nitrogen atmosphere to a temperature in the range of 80-110° C. followed by dropwise addition of 30-98% $HNO_3$ preferably 70% in four slots each after 2 hrs; and
  ii. Removing the water formed during the reaction azeotropically According to the process, to a three-necked round bottom flask fitted with reverse dean-stark apparatus is charged with an aromatic compound, an organic solvent, and the catalyst prepared by the process of instant invention. The reaction flask is flushed with nitrogen. The reaction mixture is refluxed at a temperature in the range of 80-110° C. for about an hour followed by drop wise addition of 30-98% $HNO_3$ preferably 70%. The water formed during the reaction is removed azeotropically using the reverse dean-stark apparatus. The reactions were is carried out for 8-16 hours and were monitored by GC analysis.

The aromatic compounds are selected from monocyclic or polycyclic aromatic compounds which may be monosubstituted or polysubstituted by, for example, nitro, nitroso, halogen, hydroxyl, alkoxy, aryloxy, carboxyl, alkylcarbonyloxy, arylcarbonyloxy, acylamino, alkylsulfonyl, arylsulfonyl, alkylsulfoxyl, arylsulfoxyl, sulfo, cyano and/or C1-C17alkyl groups, preferably by nitro, halogen, cyano and/or C1-C17alkyl groups. Amino, alkylamino or dialkylamino groups, low-valency sulfur- or phosphorus-containing substituents and other readily oxidizable or nitratable groups are unsuitable for the purpose of a selective nitration of the aromatic ring. Preferred aromatic hydrocarbons are unsubstituted or substituted benzene, xylenes, toluene, naphthalene, phenols, biphenyl, anthracene and phenanthrene, heteroaryls. The nitrating agent, nitric acid, is used in the molar ratio of 2 to 0.35 (conc. 30-70%) per mole of the aromatic compound used. The catalyst is used in the molar ratio of 0.009 to 0.1 per mole of the aromatic compound used.

The aromatic compound is nitrated in a solution in an organic solvent. The organic solvent is selected from solvents with a boiling point in the range of 80-110° C. such as acetonitrile, 1,2 dichloroethane, dioxane, and the like either alone or in combination thereof.

The present invention provides a conversion rate of 85-90% with selectivity in the range 30-60% depending, upon the aromatic compound used, molar ratio of catalyst used and molar ratio of nitrating agent.

The present invention discloses a process for preparation of the solid acid catalyst. Accordingly, solution of metatungstate salt in distilled water, is added to a solution of ethyl silicate-40 and C1 to C6 alcohol. The mixture is stirred for about 2-4 hrs followed by addition of 5% aqueous $NH_3$ solution. The solution is stirred further until a gelation started. Once it started slow down the stirring and kept it overnight to form white gel. The gel is air dried and calcined at about 500° C. to obtain desired product.

The metatungsate salt is selected from alkali or alkaline metals or ammonium salt.

Optionally, the process for preparation of solid state catalyst includes oxidizing tungstic acid with aq. $H_2O_2$ and neutralizing using ammonia to obtain a mixture. This is followed by adding said solution to a mixture of silica-40 and C1 to C6 alcohol, stirring, adding 2-10% ammonia to obtain a white gel. Drying and calcination at about 500° C. to yield the desired catalyst.

The catalyst $WO_3$ supported on mesoporous silica support is characterised by XRD as depicted in FIG. 1. The catalyst used in the instant invention is acidic in nature and have acidity <3. The BET surface area of the catalyst 367 to 397 $M^2/g$.

The catalyst is stable up to 5 cycles and can be recycled.

The novelty of the present invention lies in carrying out nitration of aromatics in liquid phase using $WO_3$ on mesoporous silica support with high conversion and selectivity for the desired product and with no deactivation of the solid acid catalyst. Further, the reaction can be carried out at low temperature using said catalyst.

EXAMPLES

Following examples are given by way of illustration and therefore should not be construed to limit the scope of the invention.

Example 1

Preparation of Catalyst

In a 50 mL beaker, 0.21 g ammonium metatungstate was dissolved in 7 mL distilled water. In another 250 mL beaker, a solution of ethyl silicate-40 (49.5 g) and 30 g iso-propyl alcohol was stirred for 1 h and to this solution aqueous solution of ammonium metatungstate was added dropwise. This solution was stirred for 3 h followed by addition of 5 mL 5% aqueous $NH_3$ solution. The solution was stirred until a white gel was obtained. This gel was air dried and calcined at 500° C. for 5 h.

Example 2

In a 50 mL beaker, 1.05 g ammonium metatungstate was dissolved in 7 mL distilled water. In another 250 mL beaker, a solution of ethyl silicate-40 (47.5 g) and iso-propyl alcohol (30 g) was stirred for 1 h and to this solution aqueous solution of ammonium metatungstate was added dropwise. This solution was stirred for 3 h followed by addition of 5 mL 5% aqueous $NH_3$ solution. The solution was stirred until a white gel was obtained. This gel was air dried and calcined at 500° C. for 5 h.

Example 3

In a 50 mL beaker, 2.1 g ammonium metatungstate was dissolved in 10 mL distilled water. In another 250 mL beaker, a solution of 45 g ethyl silicate-40 and 30 g iso-propyl alcohol was stirred for 1 h and to this solution aqueous solution of ammonium metatungstate was added dropwise. This solution was stirred for 3 h followed by addition of 1.4 mL 5% aqueous $NH_3$ solution. The solution was stirred till a white gel was obtained. This gel was air dried and calcined at 500° C. for 5 h.

Example 4

In a 250 mL beaker, 3.2 g ammonium metatungstate was dissolved in 10 mL distilled water. In another 250 mL beaker, a solution of 42.5 g ethyl silicate-40 and 30 g iso-propyl alcohol was stirred for 1 h and to this solution aqueous solution of ammonium metatungstate was added dropwise. This solution was stirred for 3 h followed by addition of 2.1 mL 5% aqueous ammonia solution. The solution was stirred till a white colored gel was obtained. This gel was air dried and calcined at 500° C. for 5 h.

Example 5

In a 50 mL beaker, 4.25 g ammonium metatungstate was dissolved in 10 mL distilled water. In another 250 mL beaker, a solution of 40 g ethyl silicate-40 and 30 g iso-propyl alcohol was stirred for 1 h and to this solution aqueous solution of ammonium metatungstate was added dropwise. This solution was stirred for 3 h followed by addition of 2 mL 2.5% aqueous ammonia solution. The solution was stirred until a white colored gel was obtained. This gel was air dried and calcined at 500° C. for 5 h.

Example 6

In a 250 mL beaker, 4.3 g tungstic acid was dissolved in 3 mL distilled water and 51 mL 50% aqueous hydrogen peroxide. This was followed by addition of 3 mL 25% aqueous ammonia. In another 500 mL beaker, 40 g ethyl silicate-40 and 30 g of iso-propyl alcohol was stirred for 1 h and to this solution tungstic acid solution was added dropwise. This solution was stirred for 3 h followed by addition of 0.6 mL 10% aqueous ammonia solution. The solution was stirred until a white gel was obtained. This gel was air dried and calcined at 500° C. for 5 h.

Example 7

In a 250 mL beaker, 5.69 g sodium tungstate was dissolved in 15 mL distilled water. In another 500 mL beaker, 40 g ethyl silicate-40 and 50 g of iso-propyl alcohol was stirred for 1 h and to this solution sodium tungstate solution was added dropwise. This solution was stirred for 3 h followed by addition of 3 mL 2.5% aqueous ammonia solution. The solution was stirred until a white gel was obtained. This gel was air dried and calcined at 500° C. for 5 h.

Example 8

In a 50 mL beaker, 5.31 g ammonium metatungstate was dissolved in 10 mL distilled water. In another 250 mL beaker, a solution of 37.5 g ethyl silicate-40 and 30 g iso-propyl alcohol was stirred for 1 h and to this solution aqueous solution of ammonium metatungstate was added dropwise. This solution was stirred for 3 h followed by addition of 3.5 mL 2.5% aqueous ammonia solution. The solution was stirred until it forms white gel. This gel was air dried and calcined at 500° C. for 5 h.

Example 9

In a 50 mL beaker, 6.37 g ammonium metatungstate was dissolved in 15 mL distilled water. In another 250 mL beaker, a solution of 35 g ethyl silicate-40 and 30 g iso-propyl alcohol was stirred for 1 h and to this solution; the aqueous solution of ammonium metatungstate was added dropwise. This solution was stirred for 3 h followed by addition of 4 mL 2.5% aqueous ammonia solution. The solution was stirred until it forms white gel. This gel was air dried and calcined at 500° C. for 5 h.

Example 10

Catalyst Characterization

Powder X-ray diffraction patterns of the catalysts were recorded on PAN anlytical X'Pert Pro Dual Goniometer diffractometer X'celerator solid state detector was employed for the experiments with CuKα (1.542 Å) radiation and a Ni filter (FIG. 1).

Example 11

The strength of acid sites on the catalyst was calculated by acid-base titration. Firstly, aqueous NaOH solution (0.01 mol/L, 25 mL) was added to a catalyst (0.022 g). The mixture was then stirred for 2 h at room temperature 27° C. After centrifugal separation, one drop of phenolphthalein solution was added to the filtrate and this solution was then titrated with HCl (0.01 mol/L) to neutrality (Table 1). The number of acid sites were calculated by subtracting the number of acid sites of $SiO_2$ from the desired sample.

TABLE 1

Acidity measurements of the catalysts

| Sample | Temp. ° C. | $NH_3$ desorbed ml/g | Acidity mmol/g |
|---|---|---|---|
| 5% $WO_3$/$SiO_2$ | 142.5 | 3.36 | 0.15 |
| 10% $WO_3$/$SiO_2$ | 177.2 | 13.73 | 0.61 |
| 15% $WO_3$/$SiO_2$ | 164.1 | 12.06 | 0.54 |
| 20% $WO_3$/$SiO_2$ | 201.8 | 18.43 | 0.82 |
| 25% $WO_3$/$SiO_2$ | 185.1 | 17.12 | 0.76 |
| 30% $WO_3$/$SiO_2$ | 172.1 | 12.6 | 0.56 |
| 20% $WO_3$/$SiO_2$ (TA) | 167.4 | 6.38 | 0.28 |
| 20% $WO_3$/$SiO_2$ (NaT) | 186.5 | 1.68 | 0.07 |

| Entry | Catalyst as prepared in example | Number of acid sites, mmol/g[#] |
|---|---|---|
| 1 | 1 | 0.7 |
| 2 | 2 | 1.0 |
| 3 | 3 | 0.6 |
| 4 | 4 | 0.9 |
| 5 | 5 | 2.8 |
| 6 | 6 | 2.8 |
| 7 | 7 | 1.3 |
| 8 | 8 | 2.3 |
| 9 | 9 | 2.4 |

[#]amount of acidic sites present on per gram of catalyst

Nitration of O-Xylenes

Example 13

A 250 mL three-necked round bottom flask fitted with reverse dean-stark apparatus was charged with 21.205 g o-xylene (0.2 mol), 120 mL 1,2 dichloro ethane, and 4.242 g catalyst as prepared in example 5. The flask was flushed with nitrogen. The solution was refluxed at 110° C. for 1 h. Then 16.4 mL of 70% $HNO_3$ (0.266 mol) was added to the reaction flask dropwise. The water formed during the reaction was removed azeotropically using the reverse dean-stark apparatus. The reaction was carried out for 8 h. The reaction was monitored by GC analysis. In this reaction 74.5% conversion of o-xylene was obtained with 44.8% and 53.7% 3-nitro o-xylene (3NOx) and 4-nitro o-xylene (4NOx), respectively. Other unidentified products were 1.5%.

Example 14

A 250 mL three-necked round bottom flask fitted with reverse dean-stark apparatus was charged with 10.62 g o-xylene (0.1 mol), 60 mL 1,2 dichloro ethane, and 2.12 g of catalyst as prepared in example 5. The reaction flask was flushed with nitrogen. The reaction mixture was refluxed at 110° C. for 1 h followed by the dropwise addition of 11.35 mL (0.2 mol) 70% $HNO_3$. The water formed during the reaction was removed using the reverse dean-stark apparatus. The reaction was carried out for 16 h. The reaction was monitored by GC analysis. In this reaction 94.9% conversion of o-xylene was obtained with 48.0% and 51.1% 3-nitro o-xylene (3NOx) and 4-nitro o-xylene (4NOx), respectively. Other unidentified products were 0.9%.

Example 15

The 250 mL three-necked round bottom flask fitted with reverse dean-stark apparatus was charged with 21.215 g o-xylene (0.2 mol), 120 mL 1,2 dichloro ethane, and 4.245 g of catalyst as prepared in example 5. The flask was flushed with nitrogen. The reaction mixture was refluxed at 110° C. for 1 h followed by the dropwise addition of 35.6 mL (0.266 mol) 30% $HNO_3$. The water formed during the reaction was removed using reverse dean-stark apparatus. The reaction was carried out for 8 h. The reaction was monitored by GC analysis. In this reaction 28.2% conversion of o-xylene was obtained with 47.3% and 47.3% 3-nitro o-xylene (3NOx) and 4-nitro o-xylene (4NOx), respectively. Other unidentified products were 5.4%.

Example 16

The 250 mL three-necked round bottom flask fitted with reverse dean-stark apparatus was charged with 21.215 g o-xylene (0.2 mol), 120 mL 1,2 dichloro ethane, and 4.242 g of catalyst as prepared in example 6. The flask was flushed with nitrogen. The reaction mixture was refluxed at 110° C. for 1 h followed by the dropwise addition of 35.6 mL (0.266 mol)

70% HNO$_3$. The water formed during the reaction was removed using reverse dean-stark apparatus. The reaction was carried out for 8 h. The reaction was monitored by GC analysis. In this reaction 48.2% conversion of o-xylene was obtained with 49.7% and 49.9% 3-nitro o-xylene (3NOx) and 4-nitro o-xylene (4NOx), respectively. Other unidentified products were 0.4%.

Example 17

The 250 mL three-necked round bottom flask fitted with reverse dean-stark apparatus was charged with 21.217 g o-xylene (0.2 mol), 120 mL 1,2 dichloro ethane, and 4.24 g of catalyst as prepared in example 4. The flask was flushed with nitrogen. The reaction mixture was refluxed at 110° C. for 1 h followed by the dropwise addition of 12.8 mL (0.2 mot) 70% HNO$_3$. The water formed during the reaction was removed using reverse dean-stark apparatus. The reaction was carried out for 8 h. The reaction was monitored by GC analysis. In this reaction 48.5% conversion of o-xylene was obtained with 48.2% and 51.1% 3-nitro o-xylene (3NOx) and 4-nitro o-xylene (4NOx), respectively. Other unidentified products were 0.7%.

Example 18

The 250 mL three-necked round bottom flask fitted with reverse dean-stark apparatus was charged with 21.24 g o-xylene (0.2 mol), 120 mL 1,2 dichloro ethane, and 4.245 g of catalyst as prepared in example 8. The flask was flushed with nitrogen. The reaction mixture was refluxed at 110° C. for 1 h followed by the dropwise addition of 12.8 mL (0.2 mol) 70% HNO$_3$. The water formed during the reaction was removed using reverse dean-stark apparatus. The reaction was carried out for 8 h. The reaction was monitored by GC analysis. In this reaction 46.5% conversion of o-xylene was obtained with 47.8% and 51.0% 3-nitro o-xylene (3NOx) and 4-nitro o-xylene (4NOx), respectively. Other unidentified products were 1.2%.

Example 19

The 250 mL three-necked round bottom flask fitted with reverse dean-stark apparatus was charged with 21.21 g o-xylene (0.2 mot), 120 mL 1,2 dichloro ethane, and 4.241 g of catalyst as prepared in example 9. The flask was flushed with nitrogen. The reaction mixture was refluxed at 110° C. for 1 h followed by the dropwise addition of 12.8 mL (0.2 mol) 70% HNO$_3$. The water formed during the reaction was removed using reverse dean-stark apparatus. The reaction was carried out for 8 h. The reaction was monitored by GC analysis. In this reaction 39.4% conversion of o-xylene was obtained with 48.5% and 47.3% 3-nitro o-xylene (3NOx) and 4-nitro o-xylene (4NOx), respectively. Other unidentified products were 4.16%.

Nitration of Benzene

Example 20

A 100 mL three-necked reaction flask fitted with reverse dean-stark apparatus was charged with 7.8 g benzene (0.1 mol), 60 mL 1,2 dichloro ethane, and 1.56 g of catalyst as prepared in example 5. The flask was flushed with nitrogen. The reaction mixture was refluxed at 100° C. for 1 h followed by dropwise addition of 6.42 mL (0.1 mol) of 70% HNO$_3$. The water formed during the reaction was removed using reverse dean-stark apparatus. The reaction was carried out for 8 h. The reaction was monitored by GC analysis. In this reaction 18.6% benzene conversion was obtained with 100% selectivity for mono nitro benzene.

Nitration of Toluene

Example 21

A 100 mL three-necked reaction flask fitted with reverse dean-stark apparatus was charged with 9.214 g toluene (0.1 mol), 40 mL 1,2 dichloro ethane, and 1.842 g of catalyst as prepared in example 5. The flask was flushed with nitrogen. The reaction mixture was refluxed at 100° C. for 1 h followed by dropwise addition of 8.6 mL (0.133 mol) of 70% HNO$_3$. The water formed during the reaction was removed using reverse dean-stark apparatus. The reaction was carried out for 8 h. The reaction was monitored by GC analysis. In this reaction 80.5% toluene conversion was obtained with 54.7% selectivity for 2-nitro toluene and 41.6% for 4-nitro toluene. Other products were 3.7%.

Nitration of Chlorobenzene

Example 22

A 100 mL reaction flask fitted with reverse dean-stark apparatus was charged with 11.250 g chlorobenzene (0.1 mol), 48 mL 1,2 dichloro ethane and 2.250 g of catalyst as prepared example 5. The flask was flushed with nitrogen. The reaction mixture was refluxed at 110° C. for 1 h followed by the dropwise addition of 8.6 mL (0.133 mol) 70% HNO$_3$. The water formed during the reaction was removed using fitted with reverse dean-stark apparatus. The reaction was carried out for 8 h. The reaction was monitored by GC analysis. In this reaction 55.2% conversion of chlorobenzene was obtained with 61.8% of 2-nitro chlorobenzene and 38.2% of 4-nitro chlorobenzene.

Nitration of Phenol

Example 23

A 100 mL three-necked round bottom flask fitted with reverse dean-stark apparatus was charged with 9.411 g (0.1 mol) phenol, 60 mL 1,2 dichloro ethane and 1.882 g of catalyst as prepared in example 5. The reaction flask was flushed with nitrogen. The reaction mixture was refluxed at 110° C. for 1 h followed by dropwise addition of 8.6 mL (0.133 mol) of 70% HNO$_3$. The water formed during the reaction was removed using reverse dean-stark apparatus. The reaction was carried out for 8 h. The reaction was monitored by GC analysis. In this case, 100% phenol conversion was obtained with 46.5% 2-nitro phenol and 46.5% 4-nitro phenol. Other unidentified products were 7%.

Nitration of p-Cresol

Example 24

A 100 mL reaction flask fitted with reverse dean-stark apparatus was charged with 10.804 g (0.1 mol) p-cresol, 65 mL 1,2 dichloro ethane, and 2.161 g of catalyst as prepared in example 5. The flask was flushed with nitrogen. The reaction mixture was refluxed at 110° C. for 1 h followed by dropwise addition of 8.6 mL (0.133 mol) 70% HNO$_3$. The water formed during the reaction was removed using reverse dean-stark apparatus. The reaction was carried out for 8 h. The reaction was monitored by GC analysis. In this reaction, 98.7% conversion of p-cresol was obtained with 99.1% 2-nitro p-cresol and 0.9% of other products.

ADVANTAGES OF THE INVENTION

1. Liquid phase nitration at low temperature using $WO_3$ on silica support.
2. Avoids use of sulphuric acid or the nitrating mixture thus avoiding any hazardous waste, making the process environmentally benign.
3. High conversion and selectivity towards various aromatic compounds used for nitration.

The invention claimed is:

1. A process of liquid phase nitration of aromatic compounds using a solid acid catalyst, said process comprising: Refluxing a solution of an aromatic compound and the solid acid catalyst in an organic solvent under nitrogen atmosphere at a temperature in the range of 80-110° C. for period of 1 hour followed by drop wise addition of 30-98% $HNO_3$ with removal of water formed during the reaction azeotropically; wherein said solid acid catalyst is tungsten oxide ($WO_3$) supported on mesoporous silica having BET surface area in the range of 367 to 397 $m^2/g$ and the boiling point of said organic solvent is in the range of 80-110° C. and the organic solvent is acetonitrile, 1,2 dichloroethane or dioxane.

2. The process according to claim 1, wherein said solid acid catalyst is prepared by a process comprising:
   i. Mixing ethyl silicate-40 and C1 to C6 alcohol with stirring for a period in the range of 1 to 3 hr to obtain a solution;
   ii Adding drop wise aqueous solution of metatungstate salt in the solution as obtained in step (i);
   iii Stirring the mixture as obtained in step (ii) for a period in the range of 1 to 3 hr followed by addition of 2-10% ammonium hydroxide solution to obtain a white gel; and
   iv. drying the white gel as obtained in step (iii) for period in the range of 2 to 24 hr followed by calcining for period in the range of 2 to 6 hr at temperature in the range of 450 to 500° C. at the rate of 5° C. per min to obtain the solid acid catalyst.

3. The Process according to claim 1, wherein the the aromatic compound is monocyclic or polycyclic aromatic compounds including benzene, xylene, toluene, naphthalene, phenanthrene, phenols, biphenyls, anthracene or heteroaryls.

4. The Process according to claim 3, wherein said monocyclic or polycyclic aromatic compounds are monosubstituted or polysubstituted by a group comprising nitro, nitroso, halogen, hydroxyl, alkoxy, aryloxy, carboxyl, alkylcarbonyloxy, arylcarbonyloxy, acylamino, alkylsulfonyl, arylsulfonyl, alkylsulfoxyl, arylsulfoxyl, sulfo, cyano and/or C1-C17 alkyl groups.

5. The process according to claim 1, wherein the solid acid catalyst is used in the molar ratio of 0.009 to 0.1 per mole of the aromatic compound used.

6. The process according to claim 1, further comprising
   i. Reacting the solution in water with 45 to 50% aq. hydrogen peroxide followed by addition of 20 to 30% ammonium hydroxide solution to obtain a second solution;
   ii. Adding drop wise the second solution of step (i) to a mixture of ethylsilicate-40 and C1 to C6 alcohol, stirring, and adding 2-10% ammonium hydroxide solution to obtain a white gel; and
   iii. Drying and calcining the white gel at about 500° C. to yield the desired product.

7. The process according to claim 1, wherein 70% $HNO_3$ is used for the drop wise addition.

8. The process according to claim 4, wherein the group consists of nitro, halogen, cyano and/or C1-C17 alkyl groups.

* * * * *